United States Patent [19]

Naser et al.

[11] Patent Number: 4,823,773
[45] Date of Patent: Apr. 25, 1989

[54] EXTRACORPOREAL SHOCK WAVE SOURCE WITH A PIEZOELECTRIC GENERATOR

[75] Inventors: Georg Naser, Zirndorf; Helmut Reichenberger, Eckental; Hubert Schwark, Erlangen, all of Fed. Rep. of Germany

[73] Assignee: Siemens Aktiengesellschaft, Berlin and Munich, Fed. Rep. of Germany

[21] Appl. No.: 32,603

[22] Filed: Apr. 1, 1987

[30] Foreign Application Priority Data

Apr. 1, 1986 [DE] Fed. Rep. of Germany ....... 3610818

[51] Int. Cl.<sup>4</sup> ............................. A61B 17/22
[52] U.S. Cl. ................... 128/24 A; 128/328
[58] Field of Search ............. 128/24 A, 328, 660, 128/804; 367/147

[56] References Cited

U.S. PATENT DOCUMENTS

| | | | |
|---|---|---|---|
| 4,217,516 | 8/1980 | Iinuma et al. ............ | 128/660 |
| 4,281,550 | 8/1981 | Erikson ................... | 73/626 |
| 4,526,168 | 7/1985 | Hassler et al. ............ | 128/24 A |
| 4,610,249 | 9/1986 | Makofski et al. .......... | 128/328 |

FOREIGN PATENT DOCUMENTS

| | | | |
|---|---|---|---|
| 0130709 | 1/1985 | European Pat. Off. | |
| 0148653 | 7/1985 | European Pat. Off. ........... | 128/328 |
| 847950 | 8/1952 | Fed. Rep. of Germany ...... | 128/328 |
| 3425992 | 1/1986 | Fed. Rep. of Germany ...... | 128/328 |
| 2395006 | 6/1977 | France . | |
| 2140693 | 12/1984 | United Kingdom . | |

OTHER PUBLICATIONS

"Der Ultraschall", Bergmann, pp. 374–381, 955 (1954).

*Primary Examiner*—Ruth S. Smith
*Attorney, Agent, or Firm*—Hill, Van Santen, Steadman & Simpson

[57] ABSTRACT

An extracorporeal lithotripter with a piezoceramic pressure source which emits focused pressure waves focussed at a point within a patient at which a calculus to be disintegrated is located. A number of discrete piezoceramic elements are arranged along a curve forming an ultrasound resonator having a diameter of at least about 10 cm and a radius of curvature up to about 20 cm, and operated at an ultrasound frequency below about 500 kHz. The volume between the ultrasound resonator and a terminating membrane through which the pressure waves pass is filled with a A having an acoustic impedance higher than water, preferably greater than or equal to the acoustic impedance of ethylene glycol, so that the piezoceramic elements, forming the pressure source, can be disposed closer to the focus, thereby reducing losses due to non-linear attenuation. The overall efficiency of the lithotripter is thereby increased, and the load of acoustical energy on the patient is diminished. A coupling member may be disposed between the terminating membrane and the patient.

5 Claims, 1 Drawing Sheet

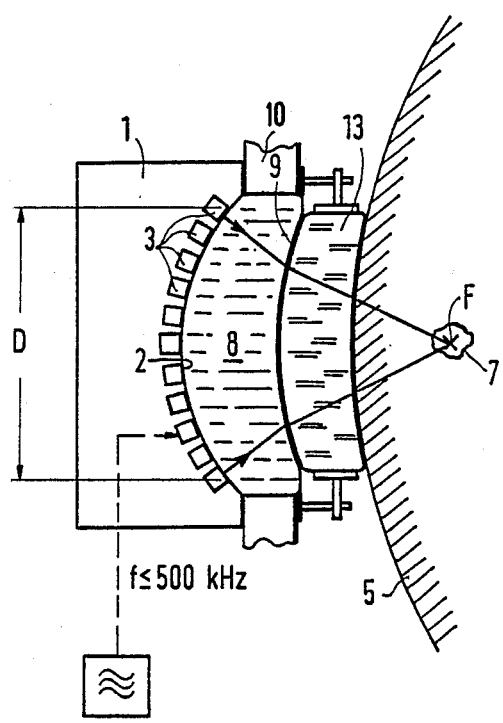

EXTRACORPOREAL SHOCK WAVE SOURCE WITH A PIEZOELECTRIC GENERATOR

BACKGROUND OF THE INVENTION

1. Field of the Invention

The present invention is directed to a shock wave source, particularly a lithotripter, having an ultrasound generator for generating a pressure wave which can be focussed to disintegrate or shatter calculi in a patient.

2. Description of the Prior Art

A lithotriper having an ultrasound generator resonator or vibrator which generates a pressure pulse and which has an approach or transmission path through which the pressure wave passes in the direction toward a patient thereby forming a "shock wave" is disclosed in German Pat. No. OS 31 19 295. In this known device, a plurality of ultrasound transducer elements are used which emit a focussed pressure wave either electronically or mechanically (by shaping). The approach path, through which the pressure wave passes, is disposed between the transducer elements and the patient, and is coupled to the patient so as to form the shock wave inside the patient for destroying calculi. The approach path is this known device is filled with water.

Piezoceramic transducer elements are preferably used in such a shock wave source. A disadvantage of piezoceramic transducer elements, however, is that a relatively steep pressure pulse is generated by the pressure source, and thus transition or "steepening" of such pressure pulse into a "shock wave" takes place relatively early, i.e., at an undesirable large distance from the focus. This is undesirable because a "shock wave," as compared to the pressure pulse, has considerable additional attenuation associated therewith due to non-linear effects. In water, such non-linear attenuation is much greater than normal linear attenuation. The resulting "shock wave" thus loses considerable energy before reaching the focus, at which the calculus to be disintegrated is isolated. Moreover, the extremely short pulse duration of the "shock wave" results in an extremely short wavelength of the fundamental oscillation. A very small focus zone, with a correspondingly small effective volume, thereby results for the disintegration of the calculus.

SUMMARY OF THE INVENTION

It is an object of the present invention to provide a shock wave source preferably suitable for use in a lithotripter, wherein the formation of the "shock wave" takes place later, i.e., at a location closer to the focus.

The above object is achieved in accordance with the principles of the present invention in a shock wave source having an ultrasound generator having a diameter of at least 10 cm and an effective radius of curvature of up to about 20 cm, and operated at an ultrasound frequency below about 500 kHz, and wherein the transmission path or volume adjacent to the emitting surface of the generator is filled with A having a higher acoustic impedance than that of water.

The shock wave source constructed in accordance with the principles of the present invention has the advantage that the pressure pulse does not form into a "shock wave" until a distance relatively close to the focus is reached. The zone of non-linear attenuation is thereby reduced. It is important, however, that the distance from the focus, at which distance the shock wave is formed, does not fall below one half of the wave length of the fundamental oscillation of the pressure pulse. If this occurs, formation of a "shock wave" would no longer be possible due to diffraction limitations.

Another advantage of the inventive shock wave source resides in the possibility of a construction of a source having a reduced length and/or an increased energy emission.

DESCRIPTION OF THE DRAWINGS

The single FIGURE shows a side view, partly in section, of a lithotripter constructed in accordance with the principles of the present invention disposed adjacent a patient.

DESCRIPTION OF THE PREFERRED EMBODIMENTS

A shock wave source constructed in accordance with the principles of the present invention is shown in the drawing. It comprises a piezoelectric pressure source 1 having a concave emission surface 2. The pressure source 1 preferably has a plurality of piezoceramic generator or ultrasound transducer elements 3 arranged on a spherical surface. The piezoceramic generator elements 3 are arranged to have (when activated) focus F, which is located inside the body of a patient 5, taking also into consideration refraction. The pressure source 1 is adjusted such that the focus location F is coincident with a calculus 7, such as a kidney stone, to be destroyed.

The piezoceramic resonators 3 are adjacent to a convex-concave transmission volume or approach path 8 closed at its front side by a terminating membrane 9 and at its circumference by a housing 10. The terminating membrane 9, the piezoceramic elements 3 and the housing 10 limit the volume of the transmission path 8. This volume is filled with a material in which sound travels at a relatively high speed $v$ and which has a relatively high density $\rho$, both in comparison to water. In particular, filling the volume of the transmission path 8 has a higher acoustic impedance $\rho v$ than water. A suitable material for filling this volume is glycerine. Also other suitable polyvalent alcohols such as ethylene glycol or other liquids may be used.

A coupling member 13 may be disposed adjacent to the concave side of the terminating membrane 9 between the transmission path 8 and the patient 5. The coupling member 13 comprises, for example, a coupling gel.

As a result of the glycerine or glycerine-like material filling the path 8, the pressure wave pulse generated by the elements 3 is transformed into a "shock wave" at a location closer to the focus F than in conventional devices having a standard water filling. Thus, the pulse is exposed to normal linear attenuation for an extended portion of the path. Loses due to non-linear attenuation of the shock wave are thereby reduced. As a result of this reduction, the piezoceramic elements 3 may be operated with a lower drive voltage. Consequently, the amplitude of the generated pressure pulse may be reduced. This in turn produces the advantage that the useful life of the piezoceramic elements 3 is increased, and the load of acoustic energy on the patient 5 is reduced as well. Alternately, given a perscribed drive voltage, limited e.g. by the voltage strength of the piezoceramic elements, the filling material having a higher acoustic impedance than water allows a more effective shock wave of higher energy to be generated.

The piezoceramic pressure source 1 may be a single large piezoceramic element, or can be a plurality of individual piezoceramic elements 3, as shown in the drawing. The pressure source 1 may either be concavely curved on its surface 2, or can be a planar transducer with which a focussing means such as, for example, a lens or a reflector, is used. Alternatively, the focussing means may be formed by a plano-concave shaping of the transmission path 8. Focussing can also be accomplished by using a plurality of ultrasound transducer elements 3, concentrically annularly arranged, the transducer elements 3 being respectively driven with time delays, so that electronic focussing is achieved.

In the embodiment shown in the drawing, the concave piezoceramic pressure source 1 has a diameter D (i.e., the distance from the upper most element 3 to the lower most element 3 as seen in the drawing) greater than 10 cm, and a radius of curvature R of up to about 20 cm. An "effective radius R of curvature" has to be considered when a source 1 having mechanical and/or electronic focussing means (as described above) is used. Such an "effective radius R" is defined by the focussing effect of such means. For generating the pressure wave pulse, the pressure source is operated at an ultrasound frequency below about 500 kHz.

Although the structure disclosed herein has been described in the form of a lithotripter, the shock wave source may also be utilized for the treatment of tumors disposed within a patient or on a patient's skin.

Although modifications and changes may be suggested by those skilled in the art, it is the intention of the inventors to embody within the patent warranted hereon, all changes and modifications as reasonably and properly come within the scope of their contribution to the art.

We claim as our invention:

1. An extracorporeal shock wave source positionable against a patient for directing shock waves at a selected focus locating within said patient, comprising:
   a piezo-electric ultrasound generator means for generating pressure pulses, said generator means having a diameter of at least about 10 cm and an effective radius of curvature for focussing of less than or equal to about 20 cm;
   means for operating said generator at an ultrasound frequency less than or equal to about 500 kHz; and
   transmission means connected between said ultrasound generator means and said patient for propagating said pressure pulses toward said focus location, said transmission means including a propagation medium selected form the group consisting of glycerine, and ethylene glycol.

2. A shock wave source as claimed in claim 1, wherein said ultrasound generator means comprises a plurality of piezoceramic ultrasound transducer elements.

3. A shock wave source as claimed in claim 1, wherein said transmission means has a convex-concave shape.

4. A shock wave source as claimed in claim 1, further comprising a coupling member abutting said transmission means and disposed between said transmission means and said patient.

5. A shock wave source as claimed in claim 1, wherein said ultrasound generator means has a pressure pulse emission surface, and wherein said emission surface is concave.

* * * * *